(12) United States Patent
Murakami et al.

(10) Patent No.: US 9,024,077 B2
(45) Date of Patent: May 5, 2015

(54) FLUORINE-CONTAINING VINYL ETHER COMPOUND AND METHOD FOR PRODUCING THE SAME

(75) Inventors: Soichiro Murakami, Ibaraki (JP); Keisuke Kokin, Ibaraki (JP); Seiichiro Murata, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 246 days.

(21) Appl. No.: 13/822,718

(22) PCT Filed: Aug. 24, 2011

(86) PCT No.: PCT/JP2011/069037
§ 371 (c)(1),
(2), (4) Date: Mar. 13, 2013

(87) PCT Pub. No.: WO2012/035942
PCT Pub. Date: Mar. 22, 2012

(65) Prior Publication Data
US 2013/0178659 A1    Jul. 11, 2013

(30) Foreign Application Priority Data

Sep. 14, 2010  (JP) ................................. 2010-205512

(51) Int. Cl.
  *C07C 43/17*   (2006.01)
  *C07C 41/09*   (2006.01)
  *C07C 41/14*   (2006.01)

(52) U.S. Cl.
  CPC ................. *C07C 43/17* (2013.01); *C07C 41/09* (2013.01); *C07C 41/14* (2013.01)

(58) Field of Classification Search
  CPC .......... C07C 43/17; C07C 41/14; C07C 41/09
  USPC ....................................................... 568/685
  See application file for complete search history.

(56) References Cited

U.S. PATENT DOCUMENTS

2008/0090977 A1   4/2008   Kokin et al.
2009/0036706 A1   2/2009   Murata et al.

FOREIGN PATENT DOCUMENTS

| CN | 101400633 A | 4/2009 |
| EP | 1760063 A1 | 4/2005 |
| JP | 2001-114718 | 4/2001 |
| JP | 2003-048857 | 2/2003 |
| JP | 2003-073321 | 3/2003 |
| WO | WO 92/05135 | 4/1992 |
| WO | WO 2005/123643 A1 | 12/2005 |
| WO | WO 2007/105633 A1 | 9/2007 |
| WO | WO 2009/151110 A1 | 12/2009 |

OTHER PUBLICATIONS

Boutevin et al., "Synthese D'Ethers Vinyliques a Chaine Laterale Fluoree", *Journal of Fluorine Chemistry*, 44, 1989, pp. 395-412.
International Search Report from corresponding PCT application No. PCT/JP2011/069037 dated Oct. 25, 2011 (2 pgs).
Höpken, Jens, et al, "Synthesis of poly(vinyl ethers)s with perflouoroalkyl pendant groups", *Makromol. Chem.* 193, 1992, pp. 275-284.
International Preliminary Report on Patentability from corresponding PCT application No. PCT/JP2011/069037 dated Apr. 18, 2013 (5 pgs).

*Primary Examiner* — Rosalynd Keys
(74) *Attorney, Agent, or Firm* — Brinks Gilson & Lione

(57) ABSTRACT

A fluorine-containing vinyl ether compound of the formula: $C_nF_{2n+1}(CH_2CF_2)_a(CF_2CF_2)_b(CH_2CH_2)_cOCH=CH_2$ is produced by subjecting a fluorine-containing alcohol of the formula: $C_nF_{2n+1}(CH_2CF_2)_a(CF_2CF_2)_b(CH_2CH_2)_cOH$ wherein n is an integer of 1 to 6, a is an integer of 1 to 4, b is an integer of 1 to 3, and c is an integer of 1 to 3, and 2-haloethyl vinyl ether of the formula: $XCH_2CH_2OCH=CH_2$ to $XCH_2CH_2OH$-elimination reaction in the presence of a palladium-based catalyst and an aliphatic amine. The fluorine-containing vinyl ether compound contain a perfluoroalkyl group having 6 or less carbon atoms, which is said to have low bioaccumulation potential.

12 Claims, No Drawings

FLUORINE-CONTAINING VINYL ETHER COMPOUND AND METHOD FOR PRODUCING THE SAME

RELATED APPLICATION

This application is a 35 U.S.C. §371 national phase filing of International Patent Application No. PCT/JP2011/069037, filed Aug. 24, 2011, through which and to which priority is claimed under 35 U.S.C. §119 to Japanese Patent Application No. 2010-205512, filed Sep. 14, 2010.

TECHNICAL FIELD

The present invention relates to a novel fluorine-containing vinyl ether compound and a method for producing the same. More particularly, the present invention relates to a novel fluorine-containing vinyl ether compound containing a perfluoroalkyl group having 6 or less carbon atoms, and a method for producing the same.

BACKGROUND ART

There is reported a method for producing fluoroalkyl vinyl ether by reacting a fluoroalkyl alcohol and alkyl vinyl ether in the presence of a palladium catalyst. However, this reaction uses large excess alkyl vinyl ether with respect to the fluoroalkyl alcohol. In addition, the time required for the reaction is 72 hours or more, and the yield is only about 75% (see Patent Document 1 and Non-Patent Document 1). Another problem is that when the crude product with a low conversion rate obtained by this reaction is purified by distillation, the high-volatile, unreacted fluoroalkyl alcohol is distilled together with the resulting product, thus making the purification operation difficult.

$$Rf(CH_2)_nOH + H(CH_2)_mOCH=CH_2 \rightarrow Rf(CH_2)_nOCH=CH_2$$

n: 2 to 6, m: 1 to 6

There is also reported a case in which the same reaction starting materials are used, and mercury acetate $Hg(OAc)_2$ is used as a catalyst. However, the yield in this case is as low as about 50%, and the use of such a mercury-based catalyst is not preferable in terms of environmental impact (see Non-Patent Document 2).

$$C_6F_{13}CH_2CH_2OH + C_2H_5OCH=CH_2 \rightarrow C_6F_{13}CH_2CH_2OCH=CH_2$$

Further, there is proposed a method for synthesizing a desired alkyl vinyl ether $R^1OCH=CH_2$ by reacting an aliphatic hydrocarbon-based alcohol $R^1OH$ ($R^1$: an alkyl group having 10 to 18 carbon atoms) and alkyl vinyl ether $R^2OCH=CH_2$ ($R^2$: an alkyl group having 1 to 4 carbon atoms) in the presence of a palladium catalyst. This reaction takes an advantage of characteristics of equilibrium reaction so that a by-product alcohol $R^2OH$ produced in the reaction and derived from the starting alkyl vinyl ether is removed from the system to shift the reaction equilibrium to the production side, thereby improving yield (see Patent Document 2).

In this reaction, however, in order to shift the equilibrium to the production side, among the starting alcohol, starting vinyl ether, target vinyl ether, and by-product alcohol present in the reaction system, the boiling point of the by-product alcohol to be removed from the system must be the lowest. For this reason, there are significant limitations not only on the structure of the target vinyl ether, but also on the structures of the starting alcohol and starting vinyl ether. Thus, this method lacks general applicability. Another problem is that the necessity of discharging the by-product alcohol outside the system makes the reactor and experimental procedures complicated, and makes simple scale-up difficult.

In addition, there is reported a method for synthesizing a corresponding alkyl vinyl ether $ROCH=CH_2$ by reacting an alcohol $ROH$ and vinyl acetate $CH_3COOCH=CH_2$ in the presence of an iridium catalyst $[Ir(cod)Cl]_2$ (see Patent Document 3). However, the iridium catalyst used in this method is expensive, and the yield of the alkyl vinyl ether to triethylene glycol as the alcohol is as low as 63% (see Example 42). This reaction is considered to be greatly affected by the acidity of alcohols.

Moreover, many of the compounds obtained here have a perfluoroalkyl group, which is rigid and therefore lacks flexibility. Thus, the side chain portion of a polymer into which this molecule is introduced lacks flexibility, and there is a possibility that the solubility of the polymer may be reduced.

Recently, hardly decomposition, high bioaccumulation potential, and suspicious biogenic toxicity of perfluorooctanoic acids (PFOAs) or perfluoroalkyl group-containing carboxylic acids (PFCAs) containing a perfluoroalkyl group having 8 or more carbon atoms are reported as environmental problems that cannot be ignored. For the vinyl ethers reported in the above documents, perfluoroalkylethyl alcohols, which are perfluorocarboxylic acid precursors, are often used as starting materials. In such a reaction, however, the possibility that the perfluoroalkylethyl alcohols may be converted into perfluorocarboxylic acids containing a perfluoroalkyl group having 8 or more carbon atoms in the environment is suggested, which is viewed as a problem. Accordingly, functional groups alternative thereto are required.

PRIOR ART DOCUMENT

Patent Document

Patent Document 1: WO 92/05135
Patent Document 2: JP-A-2001-114718
Patent Document 3: JP-A-2003-073321
Patent Document 4: WO 2007/105633
Patent Document 5: WO 2005/123643

Non-Patent Document

Non-Patent Document 1: Makromol. Chem., vol. 193, pp. 275-284 (1992)
Non-Patent Document 2: J. Fluorine Chem., vol. 44, pp. 395-412 (1989)

OUTLINE OF THE INVENTION

Problem to be Solved by the Invention

An object of the present invention is to provide a novel fluorine-containing vinyl ether containing a perfluoroalkyl group having 6 or less carbon atoms, which is said to have low bioaccumulation potential, and a method for producing the same.

Means for Solving the Problem

The present invention provides a fluorine-containing vinyl ether compound represented by the general formula:

$$C_nF_{2n+1}(CH_2CF_2)_a(CF_2CF_2)_b(CH_2CH_2)_cOCH=CH_2 \qquad [I]$$

wherein n is an integer of 1 to 6, a is an integer of 1 to 4, b is an integer of 1 to 3, and c is an integer of 1 to 3. This fluorine-containing vinyl ether compound is produced by subjecting a fluorine-containing alcohol represented by the general formula:

$$C_nF_{2n+1}(CH_2CF_2)_a(CF_2CF_2)_b(CH_2CH_2)_cOH \quad [II]$$

wherein n, a, b, and c are as defined above, and 2-haloethyl vinyl ether represented by the general formula:

$$XCH_2CH_2OCH=CH_2 \quad [III]$$

wherein X is a halogen atom, to $XCH_2CH_2OH$-elimination reaction in the presence of a palladium-based catalyst and an aliphatic amine.

Effect of the Invention

The method for producing a fluorine-containing vinyl ether compound according to the present invention provides an almost quantitative conversion rate by the use of an aliphatic amine as a polymerization inhibitor for the starting vinyl ether; therefore, the method of the present invention has the effect of improving the yield of the fluorine-containing vinyl ether compound. Moreover, as compared with alkali metal hydroxide, which is conventionally used as a polymerization inhibitor in this type of reaction, the proportion of the aliphatic amine used relative to the starting vinyl ether can be reduced by about one figure.

Conventionally reported perfluoroalkylethyl vinyl ether, upon any degradation, or $C_nF_{2n+1}$-containing compounds included as impurities may induce a possibility to chemical changes on perfluorocarboxylic acids; however, the fluorine-containing vinyl ether compound of the present invention has a perfluoroalkyl group having 6 or less carbon atoms, which has low bioaccumulation potential. Furthermore, $CH_2CF_2$ group derived from vinylidene fluoride in the molecule easily dehydrofluorination and forms a double bond, which is easily decomposed upon ozonolysis. Accordingly, the long-chain fluoroalkyl unit is expected not to remain in the environment for a long time.

Actually, the contents of a $C_8$ or more carboxylic acid and a derivative thereof in the obtained fluorine-containing vinyl ether are undetectable by LC/MS/MS analysis using a liquid chromatograph/tandem mass spectrometer.

EMBODIMENTS FOR CARRYING OUT THE INVENTION

Examples of the fluorine-containing vinyl ether compound represented by the general formula [I] include the following compounds:
$CF_3(CH_2CF_2)(CF_2CF_2)(CH_2CH_2)OCH=CH_2$
$CF_3(CH_2CF_2)_2(CF_2CF_2)(CH_2CH_2)OCH=CH_2$
$CF_3(CH_2CF_2)_4(CF_2CF_2)(CH_2CH_2)OCH=CH_2$
$CF_3(CH_2CF_2)(CF_2CF_2)_2(CH_2CH_2)OCH=CH_2$
$CF_3(CH_2CF_2)(CF_2CF_2)_3(CH_2CH_2)OCH=CH_2$
$CF_3(CH_2CF_2)(CF_2CF_2)(CH_2CH_2)_3OCH=CH_2$
$C_3F_7(CH_2CF_2)_2(CF_2CF_2)_2(CH_2CH_2)_2OCH=CH_2$
$C_4F_9(CH_2CF_2)(CF_2CF_2)_2(CH_2CH_2)OCH=CH_2$
$C_6F_{13}(CH_2CF_2)_3(CF_2CF_2)(CH_2CH_2)OCH=CH_2$
$C_6F_{13}(CH_2CF_2)_4(CF_2CF_2)_2(CH_2CH_2)_2OCH=CH_2$ Such a fluorine-containing vinyl ether compound [I] is produced by subjecting a fluorine-containing alcohol represented by the general formula [II] and 2-haloethyl vinyl ether represented by the general formula [III] to $XCH_2CH_2OH$-elimination reaction in the presence of a palladium-based catalyst and an aliphatic amine.

Examples of the fluorine-containing alcohol [II], which is one of the reaction starting materials, are shown below (see Patent Document 4).
$CF_3(CH_2CF_2)(CF_2CF_2)(CH_2CH_2)OH$
$CF_3(CH_2CF_2)_2(CF_2CF_2)(CH_2CH_2)OH$
$CF_3(CH_2CF_2)_4(CF_2CF_2)(CH_2CH_2)OH$
$CF_3(CH_2CF_2)(CF_2CF_2)_2(CH_2CH_2)OH$
$CF_3(CH_2CF_2)(CF_2CF_2)_3(CH_2CH_2)OH$
$CF_3(CH_2CF_2)(CF_2CF_2)(CH_2CH_2)_3OH$
$C_3F_7(CH_2CF_2)_2(CF_2CF_2)_2(CH_2CH_2)_2OH$
$C_4F_9(CH_2CF_2)(CF_2CF_2)_2(CH_2CH_2)OH$
$C_6F_{13}(CH_2CF_2)_3(CF_2CF_2)(CH_2CH_2)OH$
$C_6F_{13}(CH_2CF_2)_4(CF_2CF_2)_2(CH_2CH_2)_2OH$ As the 2-haloethyl vinyl ether, which is the other reaction starting material to be reacted with such a fluorine-containing alcohol, 2-haloethyl vinyl ether in which X is a halogen atom, preferably a chlorine atom or a bromine atom, more preferably a chlorine atom, is preferably used. Due to the use of 2-haloethyl vinyl ether, the reaction conversion rate thereof reaches 90% or more. The reason for this is considered as follows. Although the $XCH_2CH_2OH$-elimination reaction is a reversible reaction, the 2-haloethyl vinyl ether, which has excellent desorption performance, improves the conversion rate of the reaction and prevents the reverse reaction, thus resulting in a remarkable improvement in the reaction conversion rate. The 2-haloethyl vinyl ether is used in an amount twice or more, preferably 5 times or more, particularly preferably about 10 times, based on the molar amount of the fluorine-containing alcohol.

The $XCH_2CH_2OH$-elimination reaction between the fluorine-containing alcohol and the 2-haloethyl vinyl ether is performed in the presence of a palladium-based catalyst and an aliphatic amine.

Examples of the palladium-based catalyst include palladium (1,10-phenanthroline)acetate, palladium (2,2'-bipyridyl)acetate, palladium bis(triphenylphosphino)acetate, and the like; particularly, palladium (1,10-phenanthroline)acetate is preferably used. Such a catalyst is used in an amount of 0.5 mol % or more, particularly preferably 0.5 to 2.5 mol %, based on the fluorine-containing alcohol.

As the aliphatic amine, one that is soluble in the starting vinyl ether is used as a polymerization inhibitor for the vinyl ether. Examples thereof include monoamines having at least one hydroxyalkyl group having 1 to 4 carbon atoms, such as triethanolamine, diethanolamine, monoethanolamine, triisopropanolamine, diisopropanolamine, and monoisopropanolamine; trialkylamines containing an alkyl group having 1 to 8 carbon atoms, such as tributylamine, trihexylamine, and trioctylamine; alkylenediamines containing an alkylene group having 1 to 8 carbon atoms, such as hexamethylenediamine and octamethylenediamine; and mixtures thereof. Preferably, triethanolamine, trioctylamine, or hexamethylenediamine is used in an amount of 5 to 1000 ppm, preferably 300 to 700 ppm, based on the starting vinyl ether.

The present applicant has previously proposed a method for producing a fluorine-containing vinyl ether compound using alkali metal hydroxide (e.g., potassium hydroxide) as a polymerization inhibitor (see Patent Document 5). However, alkali metal hydroxide is almost insoluble in organic solvents, and its effect is restrictive. Therefore, a further improvement in yield has been desired. In contrast, the present invention uses the above-mentioned amine as a polymerization inhibitor, thereby achieving a further improvement in yield with a lower proportion of the amine.

The reaction is carried out without a solvent, but a solvent may be used. In this case, hydrocarbon-based solvents, such as toluene and xylene, and cyclic ether-based solvents, such as tetrahydrofuran and 1,4-dioxane, may be used in an adequate amount.

Although the reaction temperature is not particularly limited, the reaction is generally carried out at room temperature to 80° C., particularly preferably 40° C. to 70° C.

The unreacted 2-haloethyl vinyl ether, the 2-haloethanol as a by-product, and the target fluorine-containing vinyl ether compound are purified by fractional distillation. Those having a larger molecular weight and a higher boiling point are purified by molecular distillation, and then subjected to reactions, such as polymerization.

EXAMPLES

The following describes the present invention with reference to Examples.

Example 1

In a nitrogen atmosphere, 341 g (0.646 mol) of 3,3,4,4,5,5,6,6,7,7,9,9,10,10,11,11,12,12,12-nonadecafluorododecanol $C_4F_9(CH_2CF_2)(CF_2CF_2)_2(CH_2CH_2)OH$ (the contents of $C_8$ or more perfluorocarboxylic acid and a derivative thereof determined by LC/MS/MS analysis were not greater than 10 ppb, which was the detection limit), 2.4 g (0.006 mol; 1.0 mol % based on nonadecafluorododecanol) of palladium (1,10-phenanthroline)acetate, and 0.34 g (0.002 mol; 500 ppm based on 2-chloroethyl vinyl ether) of triethanolamine were added to 688 g (6.46 mol) of 2-chloroethyl vinyl ether, and the mixture was stirred at 65° C. for 8 hours. Unreacted 2-chloroethyl vinyl ether was distilled off under reduced pressure, thereby obtaining 377 g (90.1 GC %) of 3,3,4,4,5,5,6,6,7,7,9,9,10,10,11,11,12,12,12-nonadecafluorododecyl vinyl ether $C_4F_9(CH_2CF_2)(CF_2CF_2)_2(CH_2CH_2)OCH=CH_2$. The yield was 95%.

The thus obtained nonadecafluorododecyl vinyl ether was purified by distillation to a purity of 91 GC % or more using a distillation apparatus equipped with a vacuum pump. The results of $^1$H-NMR and $^{19}$F-NMR confirmed that the purified reaction product was a compound represented by the following formula. The contents of $C_8$ or more perfluorocarboxylic acid and a derivative thereof determined by LC/MS/MS analysis were not detected at all.

$C_4F_9(CH_2CF_2)(CF_2CF_2)_2(CH_2CH_2)OCH=CH_2$ $^1$H-NMR (d-acetone, TMS): ppm 6.58 to 6.41, 4.29 to 4.24 (CH=C$\underline{H}_2$)
    4.08 to 4.04 (C$\underline{H}$=CH$_2$, CH$_2$C$\underline{H}_2$)
    2.71 to 2.55 (C$\underline{H}_2$CH$_2$)
    3.59 to 3.48 (CF$_2$C$\underline{H}_2$CF$_2$)
$^{19}$F-NMR (d-acetone, C$_6$F$_6$): ppm −80.34 to −79.94 (C$\underline{F}_3$)
    −124.9 (CF$_3$C$\underline{F}_2$CF$_2$CF$_2$)
    −122.69 to −122.59 (CF$_3$CF$_2$C$\underline{F}_2$CF$_2$, CF$_2$CF$_2$CF$_2$C$\underline{F}_2$CF$_2$CH$_2$)
    −110.34 (CF$_3$CF$_2$CF$_2$C$\underline{F}_2$, C$\underline{F}_2$CF$_2$CF$_2$CF$_2$CF$_2$CH$_2$)
    −120.26 (CF$_2$C$\underline{F}_2$CF$_2$CF$_2$CF$_2$CH$_2$)
    −121.93 (CF$_2$CF$_2$C$\underline{F}_2$CF$_2$CF$_2$CH$_2$)
    −112.81 to 112.17 (CF$_2$CF$_2$CF$_2$CF$_2$C$\underline{F}_2$CH$_2$)

Example 2

In Example 1, 0.48 g (0.001 mol; 700 ppm based on 2-chloroethyl vinyl ether) of trioctylamine was used in place of 0.34 g (0.002 mol; 500 ppm based on 2-chloroethyl vinyl ether) of triethanolamine, thereby obtaining 378 g (89.0 GC %) of 3,3,4,4,5,5,6,6,7,7,9,9,10,10,11,11,12,12,12-nonadecafluorododecyl vinyl ether $C_4F_9(CH_2CF_2)(CF_2CF_2)_2(CH_2CH_2)OCH=CH_2$. The yield was 94%.

Comparative Example

In a nitrogen atmosphere, 400 g (0.757 mol) of 3,3,4,4,5,5,6,6,7,7,9,9,10,10,11,11,12,12,12-nonadecafluorododecanol $C_4F_9(CH_2CF_2)(CF_2CF_2)_2(CH_2CH_2)OH$, 15.4 g (0.038 mol; 5.0 mol % based on nonadecafluorododecanol) of palladium (1,10-phenanthroline)acetate, and 0.4 g (0.007 mol; 500 ppm based on 2-chloroethyl vinyl ether) of potassium hydroxide were added to 807 g (7.57 mol) of 2-chloroethyl vinyl ether, and the mixture was stirred at room temperature for 72 hours. Unreacted 2-chloroethyl vinyl ether was distilled off under reduced pressure, thereby obtaining 490 g (75.2 GC %) of 3,3,4,4,5,5,6,6,7,7,9,9,10,10,11,11,12,12,12-nonadecafluorododecyl vinyl ether $C_4F_9(CH_2CF_2)(CF_2CF_2)_2(CH_2CH_2)OCH=CH_2$. The yield was 88%.

The yield of the Comparative Example, which used potassium hydroxide as a polymerization inhibitor, was only 88%. In contrast, the yield of Example 1, which used triethanolamine as a polymerization inhibitor, was 95%, and the yield of Example 2, which used trioctylamine, was 90%. It was thus confirmed that the use of an aliphatic amine as a polymerization inhibitor enhanced yield and purity.

INDUSTRIAL APPLICABILITY

The fluorine-containing vinyl ether compound of the present invention, which has a high fluorine content, has a low refractive index and is applicable to anti-reflection films for displays, and clad materials, such as optical fibers. Moreover, owing to its high fluorine content, the fluorine-containing vinyl ether compound of the present invention can be used, for example, in crosslinking agents and modifiers for various resins to improve or modify the various physical properties of the resins, such as hardness, strength, heat resistance, weather resistance, and chemical resistance. Furthermore, taking advantage of its surface-active properties, the fluorine-containing vinyl ether compound of the present invention can also be used as a component for forming water- and oil-repellents, various surface coating agents, various mold-release coating agents, and surface modifiers.

The invention claimed is:

1. A novel fluorine-containing vinyl ether compound represented by the general formula:

$$C_nF_{2n+1}(CH_2CF_2)_a(CF_2CF_2)_b(CH_2CH_2)_cOCH=CH_2 \quad [I]$$

wherein n is an integer of 1 to 6, a is an integer of 1 to 4, b is an integer of 1 to 3, and c is an integer of 1 to 3.

2. The novel fluorine-containing vinyl ether compound according to claim 1, wherein the contents of a carboxylic acid containing a perfluoroalkyl group having 8 or more carbon atoms and a derivative thereof are undetectable by LC/MS/MS.

3. A method for producing the novel fluorine-containing vinyl ether compound according to claim 1, the method comprising subjecting a fluorine-containing alcohol represented by the general formula:

$$C_nF_{2n+1}(CH_2CF_2)_a(CF_2CF_2)_b(CH_2CH_2)_cOH \quad [II]$$

wherein n is an integer of 1 to 6, a is an integer of 1 to 4, b is an integer of 1 to 3, and c is an integer of 1 to 3, and 2-haloethyl vinyl ether represented by the general formula:

$$XCH_2CH_2OCH=CH_2 \quad [III]$$

wherein X is a halogen atom, to XCH2CH2OH-elimination reaction in the presence of a palladium-based catalyst and an aliphatic amine polymerization inhibitor.

4. The method for producing the novel fluorine-containing vinyl ether compound according to claim 3, wherein the 2-haloethyl vinyl ether is used in an amount twice or more based on the molar amount of the fluorine-containing alcohol.

5. The method for producing the novel fluorine-containing vinyl ether compound according to claim 3, wherein the 2-haloethyl vinyl ether is 2-chloroethyl vinyl ether or 2-bromoethyl vinyl ether.

6. The method for producing the novel fluorine-containing vinyl ether compound according to claim 3, wherein the aliphatic amine is a monoamine containing at least one hydroxyalkyl group having 1 to 4 carbon atoms, a trialkylamine containing an alkyl group having 1 to 8 carbon atoms, or an alkylenediamine containing an alkylene group having 1 to 8 carbon atoms.

7. The method for producing the novel fluorine-containing vinyl ether compound according to claim 6, wherein the aliphatic amine is triethanolamine, trioctylamine, or hexamethylenediamine.

8. The method for producing the novel fluorine-containing vinyl ether compound according to claim 3, wherein the aliphatic amine is used in an amount of 5 to 1,000 ppm based on the starting vinyl ether.

9. The method for producing the novel fluorine-containing vinyl ether compound according to claim 3, wherein the palladium-based catalyst is palladium (I,10-phenanthroline)acetate, palladium (2,2'-bipyridyl)acetate, or palladium bis(triphenylphosphino)acetate.

10. The method for producing the novel fluorine-containing vinyl ether compound according to claim 3, wherein the palladium-based catalyst is used in an amount of 0.5 to 2.5 mol % based on the fluorine-containing alcohol.

11. The method for producing the novel fluorine-containing vinyl ether compound according to claim 6, wherein the aliphatic amine is used in an amount of 5 to 1,000 ppm based on the starting vinyl ether.

12. The method for producing the novel fluorine-containing vinyl ether compound according to claim 9, wherein the palladium-based catalyst is used in an amount of 0.5 to 2.5 mol % based on the fluorine-containing alcohol.

* * * * *